(12) United States Patent
Dhaniyala et al.

(10) Patent No.: US 9,970,855 B2
(45) Date of Patent: May 15, 2018

(54) MINIATURE ELECTRICAL AEROSOL SPECTROMETER

(71) Applicants: Suresh Dhaniyala, Potsdam, NY (US); Ishara Jayasuriya, Potsdam, NY (US)

(72) Inventors: Suresh Dhaniyala, Potsdam, NY (US); Ishara Jayasuriya, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 0 days. days.

(21) Appl. No.: 15/295,278

(22) Filed: Oct. 17, 2016

(65) Prior Publication Data
US 2017/0108425 A1    Apr. 20, 2017

Related U.S. Application Data

(60) Provisional application No. 62/241,790, filed on Oct. 15, 2015.

(51) Int. Cl.
*G01N 15/02* (2006.01)
*G01N 15/00* (2006.01)

(52) U.S. Cl.
CPC . *G01N 15/0266* (2013.01); *G01N 2015/0003* (2013.01)

(58) Field of Classification Search
CPC .................................................. G01N 15/0266
See application file for complete search history.

(56) References Cited

U.S. PATENT DOCUMENTS

| 7,298,486 | B2 * | 11/2007 | Wang | G01N 15/0266 324/71.4 |
| 8,301,396 | B1 | 10/2012 | Dhaniyala et al. | |
| 8,966,958 | B2 * | 3/2015 | Olfert | G01N 15/0255 73/28.01 |
| 9,638,665 | B2 * | 5/2017 | Gorbunov | G01N 27/622 |
| 9,753,013 | B2 * | 9/2017 | Brechtel | G01R 29/24 |

* cited by examiner

*Primary Examiner* — Jewel V Dowtin
(74) *Attorney, Agent, or Firm* — Bond Schoeneck & King, PLLC; George McGuire; Blaine Bettinger

(57) ABSTRACT

A miniature electrical-mobility aerosol spectrometer comprising a 3D-printed body comprising: (i) a single inlet section configured to receive particles to be evaluated by the spectrometer; (ii) an electrostatic precipitator section coupled to the electrostatic precipitator section; (iii) a classifier section, wherein the electrostatic precipitator section is coupled to the classifier section; and (iv) an outlet, wherein the classifier section is coupled to the outlet; a high voltage classifier plate positioned within the classifier section; and a classifier component positioned within the classifier section opposite the high voltage classifier plate, wherein the classifier component comprises sensing circuitry configured to detect particles in the classifier section, and wherein the classifier section comprises a two-sided printed circuit board, wherein the two-sided printed circuit board comprises the sensing circuitry, and wherein a first side of the two-sided printed circuit board comprises a plurality of printed collection plates.

20 Claims, 11 Drawing Sheets

MINIATURE ELECTRICAL AEROSOL SPECTROMETER

CROSS-REFERENCE TO RELATED APPLICATIONS

This application claims priority to U.S. Provisional Patent Application Ser. No. 62/241,790, filed on Oct. 15, 2016, and entitled "Design and Performance Improvements of the Miniature Electrical Aerosol Spectrometer (MEAS)," the entire disclosure of which is incorporated herein by reference.

FIELD OF THE INVENTION

The present disclosure is directed generally to aerosol spectrometers and in particular to improvements in miniature electrical aerosol spectrometry.

BACKGROUND

The role of ultrafine particles (UFPs) from a human health perspective is increasingly being recognized, and the interaction of these particles with their environment is dependent on, among other parameters, their size and number concentration. Size distribution measurements of ultrafine particles can be made using commercially available scanning electrical mobility spectrometers (SEMS). The scanning electrical mobility spectrometer technique uses a differential mobility analyzer (DMA) to classify particles based on their electrical mobility, and the concentration of the classified particles is typically measured using a condensation particle counter (CPC). In scanning electrical mobility spectrometer instruments, the voltage required for particle classification is exponentially varied to obtain size distributions in a relatively short time (~5 minutes or less). Faster size distribution measurements are possible by combining the electrical-mobility classification technique with an electrometer detector array. The availability of commercial instruments has made ambient ultrafine particles measurements possible in near real-time and at high size resolution.

Accurate estimation of human health effect of ultrafine particles requires size distribution measurements considering their spatial and temporal variability. Such measurements require the deployment of instruments over a large number of sites or on a mobile platform, but the large cost, size, and power requirements of the existing instruments make such deployments difficult. Existing portable instruments provide a measure of ultrafine number concentration, but no sizing information, or provide inefficient size information.

Accordingly, there is a continued need in the art for systems and methods that facilitate real-time, size-resolved ultrafine particles measurements.

SUMMARY OF THE INVENTION

The present disclosure is directed to inventive systems and methods for an improved Miniature Electrical Aerosol Spectrometer (MEAS). A typical MEAS comprises: (i) an inlet section; (ii) an electrostatic precipitator section; (iii) a classifier section; and (iv) an outlet. The spectrometer comprises a high voltage classifier plate and one or more collection plates within the classifier section. Appropriately selecting the shape of the collection plate can result in a sensor response that has predetermined particle size dependence. The classifier section comprises a series of collection plates printed directly on a printed circuit board. Many other configurations are possible as described or otherwise envisioned herein.

Generally in one aspect, a miniature electrical-mobility aerosol spectrometer is provided. The miniature electrical-mobility aerosol spectrometer includes: (i) a single inlet section configured to receive particles to be evaluated by the spectrometer; (ii) an electrostatic precipitator section, wherein the inlet section is coupled to the electrostatic precipitator section; (iii) a classifier section, wherein the electrostatic precipitator section is coupled to the classifier section, and further wherein the classifier comprises a high voltage classifier plate and an opposing classifier component; (iv) a sensing circuitry coupled to the classifier component and configured to detect particles in the classifier section; and (v) an outlet, wherein the classifier section is coupled to the outlet; wherein the classifier component comprises a two-sided printed circuit board, wherein the two-sided printed circuit board comprises the sensing circuitry, and wherein a first side of the two-sided printed circuit board comprises a plurality of printed collection plates.

According to an embodiment, the miniature electrical-mobility aerosol spectrometer comprises a 3D-printed body.

According to an embodiment, the electrostatic precipitator section comprises multiple channels. According to an embodiment, the electrostatic precipitator section comprises a single channel.

According to an embodiment, each of the plurality of printed collection plates is rectangular. According to an embodiment, each of the plurality of printed collection plates is round. According to an embodiment, each collection plate is spaced from its respective one or more neighboring collection plates.

According to an embodiment, a second side of the two-sided printed circuit board comprises a triax-connector.

According to an embodiment, the shape of each of the plurality of printed collection plates results in a sensor response with a predetermined particle size dependence.

According to an aspect is a miniature electrical-mobility aerosol spectrometer. The miniature electrical-mobility aerosol spectrometer includes a 3D-printed body comprising: (i) a single inlet section configured to receive particles to be evaluated by the spectrometer; (ii) an electrostatic precipitator section, wherein the inlet section is coupled to the electrostatic precipitator section; (iii) a classifier section, wherein the electrostatic precipitator section is coupled to the classifier section; and (iv) an outlet, wherein the classifier section is coupled to the outlet. The miniature electrical-mobility aerosol spectrometer further includes a high voltage classifier plate positioned within the classifier section; and a classifier component positioned within the classifier section opposite the high voltage classifier plate, wherein the classifier component comprises sensing circuitry configured to detect particles in the classifier section, and wherein the classifier section comprises a two-sided printed circuit board, wherein the two-sided printed circuit board comprises the sensing circuitry, and wherein a first side of the two-sided printed circuit board comprises a plurality of printed collection plates.

These and other aspects and embodiments of the invention will be described in greater detail below, and can be further derived from reference to the specification and figures.

BRIEF DESCRIPTION OF THE DRAWINGS

The present invention will be more fully understood and appreciated by reading the following Detailed Description in conjunction with the accompanying drawings, in which.

DETAILED DESCRIPTION OF EMBODIMENTS

The present disclosure describes various embodiments of and methods for a Miniature Electrical Aerosol Spectrometer (MEAS). More generally, Applicant has recognized and appreciated that it would be beneficial to provide a MEAS with improved efficiency and capabilities. Typically, a MEAS can have a rectangular cross-section with two main regions: the Electrostatic Precipitator (ESP) and Classifier sections. The electrostatic precipitator section enables charged particle injection into the classifier section in a narrow range of streamlines at the desired location. The injected charged particles are then segregated based on their electrical mobility in the classifier section and collected on a series of plates that are connected to electrometers. Realtime particle size distribution measurements can be inferred from the electrometer signal strengths with the knowledge of the instrument transfer function. A theoretical approach is developed to calculate the MEAS transfer function considering the non-uniformity in the electric and flow fields inside the instrument, and accounting for the instrument dimensions and its operating conditions. The theoretical predictions of size classification characteristics are seen to compare well with numerical results. The modeling results suggest that an optimal operational domain exists for Miniature Electrical Aerosol Spectrometer.

Accordingly, a MEAS typically has: (i) an inlet section; (ii) an electrostatic precipitator section; (iii) a classifier section; and (iv) an outlet. According to an embodiment, the spectrometer can further include a plurality of upstream plates within the electrostatic precipitator section and a plurality of electrostatic precipitator plates within the precipitator section. According to an embodiment, the spectrometer can further include a high voltage classifier plate and one or more collection plates within the classifier section. Appropriately selecting the shape of the collection plate can result in a sensor response that has predetermined particle size dependence.

According to an embodiment, the spectrometer comprises a transfer function that determines an optimum configuration of the electrostatic precipitator section and the classifier section. The transfer function includes a series of calculations to account for certain non-linear characteristics of an electric field generated within the spectrometer.

An optimal design of the MEAS requires theoretical understanding of particle behavior in the instrument as a function of its physical dimensions and operating environment. For more information about the theory and operation of a MEAS, see U.S. Pat. No. 8,301,396 ("Miniature Ultrafine Particle Sensor") by Dhanijala and Ranjan, the entire contents of which are incorporated herein by reference.

Figure 1:
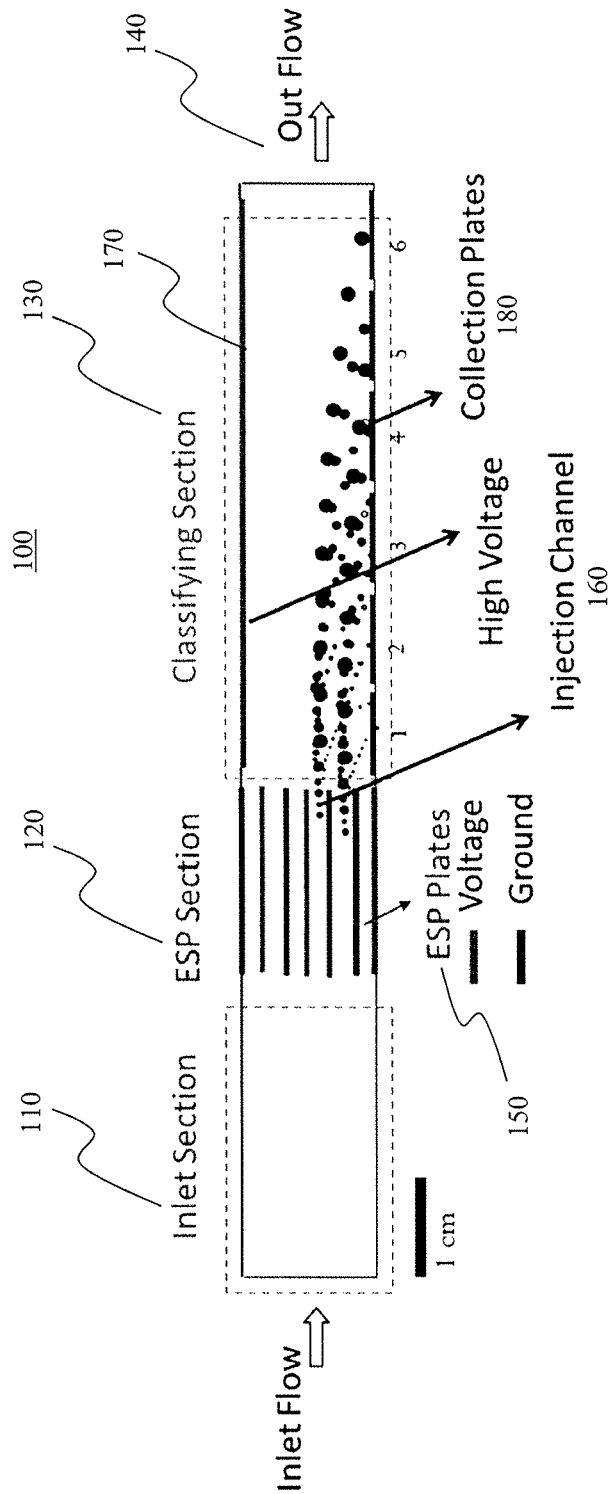
FIG. 1 is a schematic representation of a Miniature Electrical Aerosol Spectrometer (MEAS), in accordance with an embodiment.

Referring to FIG. 1, in one embodiment, is a Miniature Electrical Aerosol Spectrometer (MEAS) 100. Although this MEAS comprises a rectangular cross-section, many different shapes, sizes, and cross-sections are possible. MEAS 100 comprises an input 110, an electrostatic precipitator section (ESP) 120, a classifier section 130, and an output 140. According to an embodiment, particles are charged upstream of the MEAS in a bipolar diffusion charger and then sampled into the MEAS 100 via the input 110. Once in the MEAS 100, the sampled particles first pass through the electrostatic precipitator section 120. According to an embodiment, the ESP comprises a set of parallel plates (ESP Plates 150 as illustrated in FIG. 1) that act as electrostatic precipitators when a potential difference is applied across them. The different plates can be individually maintained at different voltage potentials. The parameters of the electrostatic precipitator section, i.e., number of plates, plate spacing, length, and channel potential difference, are chosen such that charged particles with highest electrical mobility can be electrostatically precipitated through the desired channels. For example, as shown in the embodiment in FIG. 1, the ESP Plates 150 are alternating voltage and ground. According to an embodiment, one set of the ESP Plates 150 are both the same polarity and hence transmit charged particles.

Across one selected electrostatic precipitator channel, called an injection channel 160, a zero potential difference is maintained to permit the passage of charged particles into a narrow flow region in the classifier section 130. The minimum length of the electrostatic precipitator channel plates is determined by the flow velocity, the available potential difference, and the largest particle mobility to be captured. The smallest spacing between the channels is determined by the breakdown voltage for the operating environmental conditions. The flow through of the non-injection electrostatic precipitator channels acts as sheath flow in the classifier section.

In the classifier section 130, a potential difference can be maintained to segregate the injected particles by their electrical mobility. This section consists of a classifier plate 170 maintained at high voltage and a set of collection plates connected to one or more electrometers (not shown). Charged particles condense out of the flow and are trapped on the collection plates 180 (plates 1-6 as illustrated in FIG. 1).

Uncharged particles entering through the different electrostatic precipitator channels will exit the classifier section 130 unaffected by the applied electric field, via outlet 140. Electrometers (not shown) connected to the collection plates will output current signals proportional to the number of charged particles trapped on the plates. For real-time particle size distribution measurement, an array of electrometers is deployed along the length of the flow. The particle sizing characteristics of the MEAS 100 depends on the choice of the injection channel, dimensions of the classifier section 104, voltage on the classifier plate, number of injection channels and collection plates, and average flow velocity.

According to an embodiment, the inlet 110 of the MEAS may be required to transition the flow from a circular cross-section to the rectangular cross-section at the entrance of the electrostatic precipitator section. To minimize recirculation regions, the inlet section can be designed to gradually change from a circular to a rectangle cross-section. An optimal expansion angle of ~7 degrees will minimize recirculation within the inlet, but this will result in an impractically long section. Instead, an expansion angle of 18 degrees can be chosen and a wire mesh is located in the middle of the 10 cm long section to provide pressure drop and promote flow uniformity across inlet section exit.

According to an embodiment, the electrostatic precipitator section can be designed with five parallel electropolished stainless steel plates that are 2 cm long, 5 cm wide, and 0.7 mm thick, and spaced 2 mm apart. However, many other number and sizes of plates are possible. For electrical connectivity, the plates can be individually connected to electrical wires through a screw and spring setup on the sides of the instrument. An ultraminiature voltage amplifier can be used to set the voltage on the electrostatic precipitator plates. The electrostatic precipitator plate voltages can be chosen such that charged particles are electrostatically filtered through all the electrostatic precipitator channels except one selected injection channel. For typical operation, the potential difference in the electrostatic precipitator channels must result in the capture of sub-500 nm singly-charged particles, while remaining below the breakdown potential. A high voltage source is used through a voltage distributor to set voltages on the electrostatic precipitator plates. For handling safety, the electrostatic precipitator section and classifier section are housed in an external insulated unit.

According to an embodiment, the classifier section of the MEAS consists of a set of five collection plates, spaced 1 mm apart, located across a classifier plate that is maintained at high voltage. Electropolished stainless steel rectangular plates of 1 cm length, 5 cm width, and 0.7 mm thickness are used as collection plates.

According to an embodiment, increasing the number of channels will allow for higher resolution measurements. The number of channels determines the fraction of flow with charged particles entering the classification region. Increasing the channels will, however, increase the cost of operation, because of higher pressure drop in the instrument.

According to an embodiment, the net electrometer signal ($E_i$) of $i^{th}$ collection plate is related to the size distribution ($dN/d \log D_p$) and the operating conditions as set forth in the following equation:

$$E_i = Q_a e \sum_n n \int_0^\infty f_c(D_p, n) \Omega_i(Z_p) \frac{dN}{d \log D_p} d \log D_p \qquad \text{(Eq. 1)}$$

Figure 2:
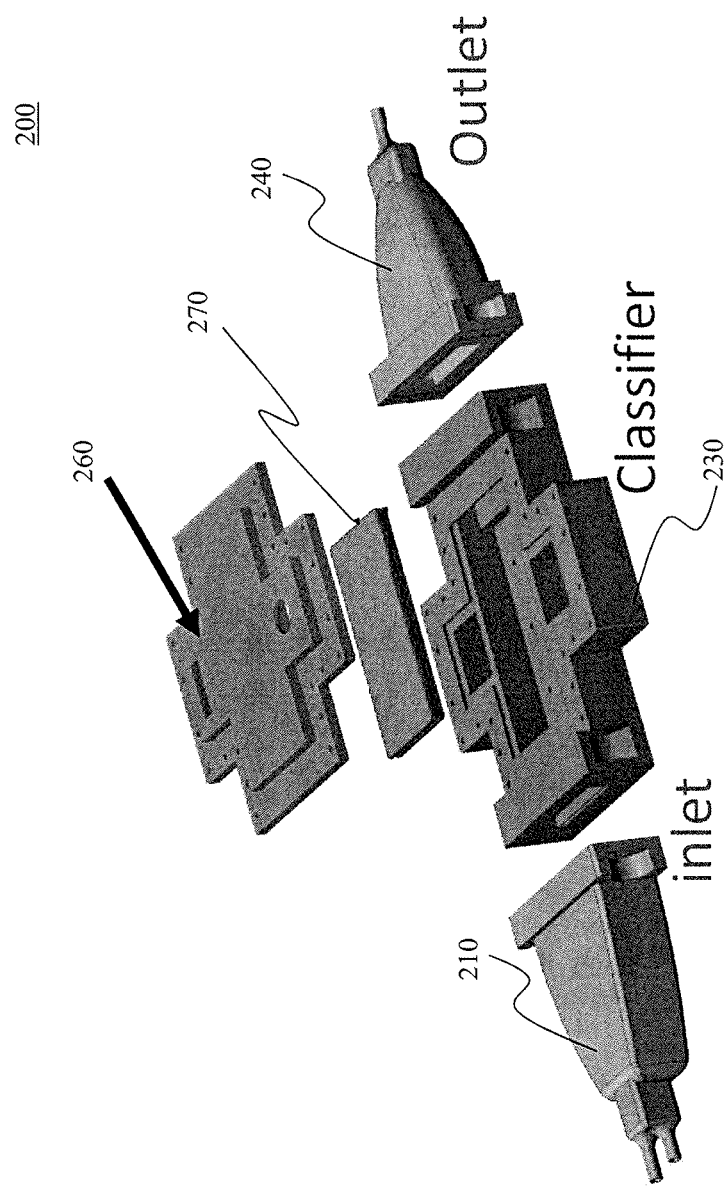
FIG. 2 is a schematic representation of a Miniature Electrical Aerosol Spectrometer, in accordance with an embodiment.

Referring to FIG. 2, in one embodiment is a Miniature Electrical Aerosol Spectrometer (MEAS) 200. MEAS 200 comprises an inlet 210, a classifier 230, and an outlet 240. According to an embodiment, particles are charged upstream of the MEAS in a bipolar diffusion charger and then sampled into the MEAS 200 via the inlet 210. Once in the MEAS 200, the particles pass into the classifier 230, where a potential difference can be maintained to segregate the injected particles by their electrical mobility. This section consists of a classifier plate 270 maintained at high voltage and a set of collection plates. Charged particles condense out of the flow and are trapped on the collection plates. Uncharged particles entering through the different electrostatic precipitator channels will exit the classifier section 130 unaffected by the applied electric field, via outlet 140. Electrometers connected to the collection plates will output current signals proportional to the number of charged particles trapped on the plates. For real-time particle size distribution measurement, an array of electrometers is deployed along the length of the flow.

Figure 3:
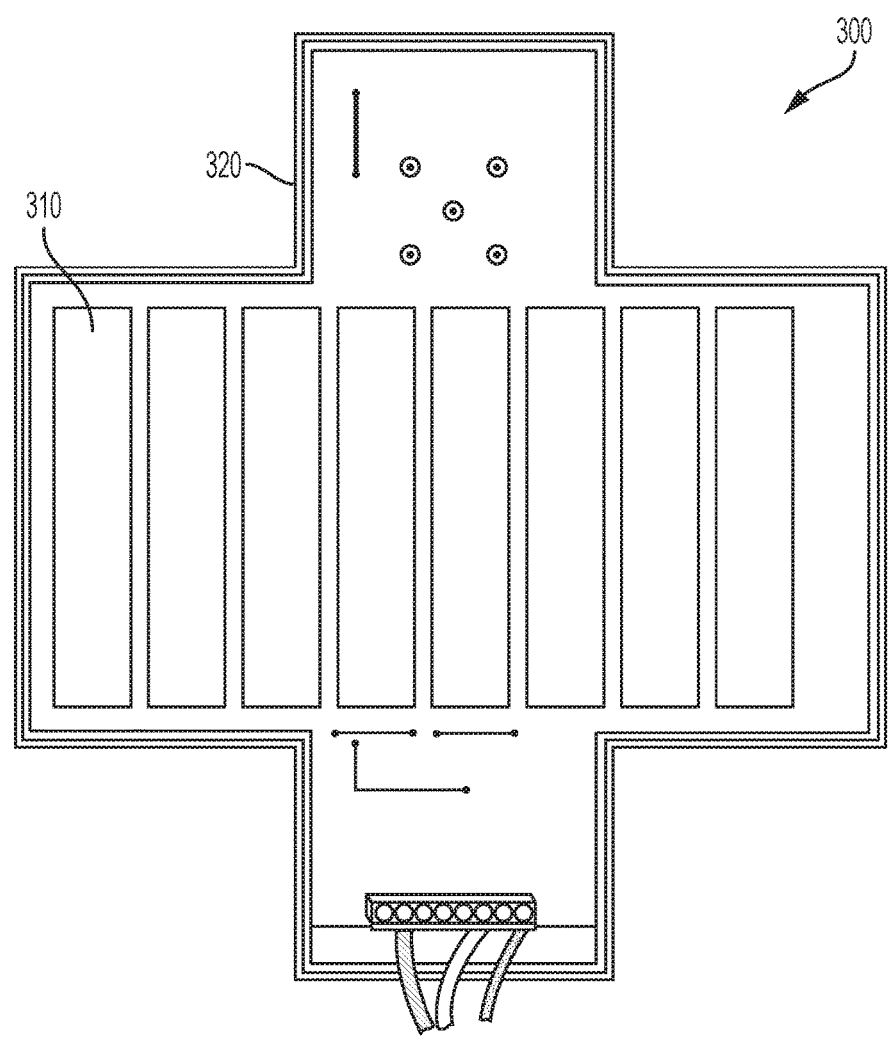
FIG. 3 is an image of a first side of a classifier component of a Miniature Electrical Aerosol Spectrometer, in accordance with an embodiment.
Figure 4:
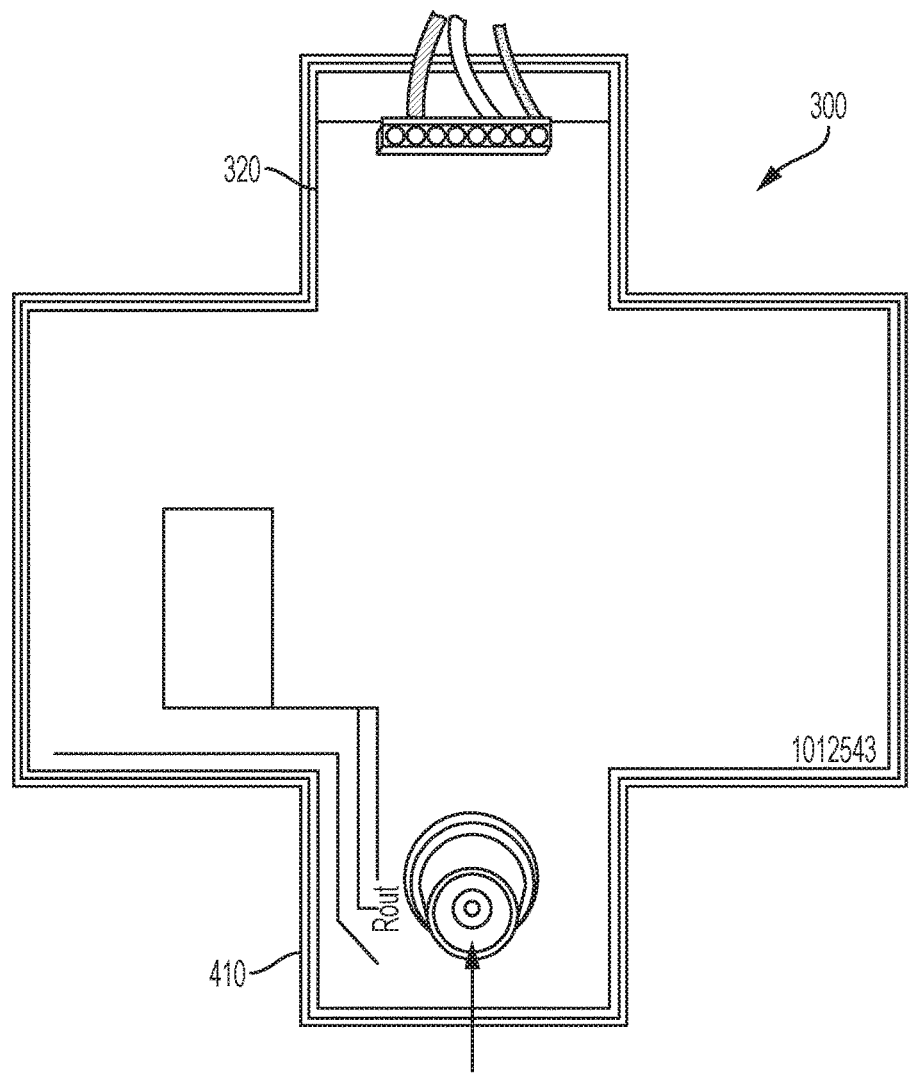
FIG. 4 is an image of a second side of a classifier component of a Miniature Electrical Aerosol Spectrometer, in accordance with an embodiment.

Referring to FIG. 3, in one embodiment, is a collection component 300, which comprises a series of collection plates 310 (here, there are eight (8) plates, although the number is highly variable) printed directly on a printed circuit board 320. According to an embodiment, the printed circuit board 320 can be FR-4, or any other grade or type of circuit board material. Referring to FIG. 4 is a reverse view of the collection component 300 in FIG. 3. The collection component 300 comprises the printed circuit board 320, and optionally comprises a triax-connector 410 for external electrometer measurements.

Printing the plurality of collection plates 310 directly on the printed circuit board 320 provides numerous improvements over prior MEAS designs. For example, the collection component 300 can be created using 3D-printing techniques, thereby saving time and expense. The collection component 300 will also be lightweight and portable. Additionally, there is faster and more efficient manufacturing of complicated shapes of the inlet, ESP, and classification regions. For example, printing the collection plates 310 directly on the printed circuit board 320 allows for precise location, complex shapes, and electrical isolation while being inexpensive.

Indeed, portions or all of the MEAS 100 or 200 can be 3D-printed. A polymer that results in a durable, waterproof, and/or affordable device can be utilized. For example, according to one embodiment the instrument is printed using a photopolymer based material such as Somos® WaterShed material, among many other polymers. This results in acceptable finish quality, good moisture resistance, and reasonable strength and dielectric properties.

According to another embodiment, the collection component 300 integrates the collection plates 310 and the sensing circuitry. This results in low-cost manufacturing, many different possible designs for the collection plates, and reduced signal transportation noise. Further, the printed collection plates capture particles over a narrow size range with minimal leakage currents between the channels.

Figure 5:
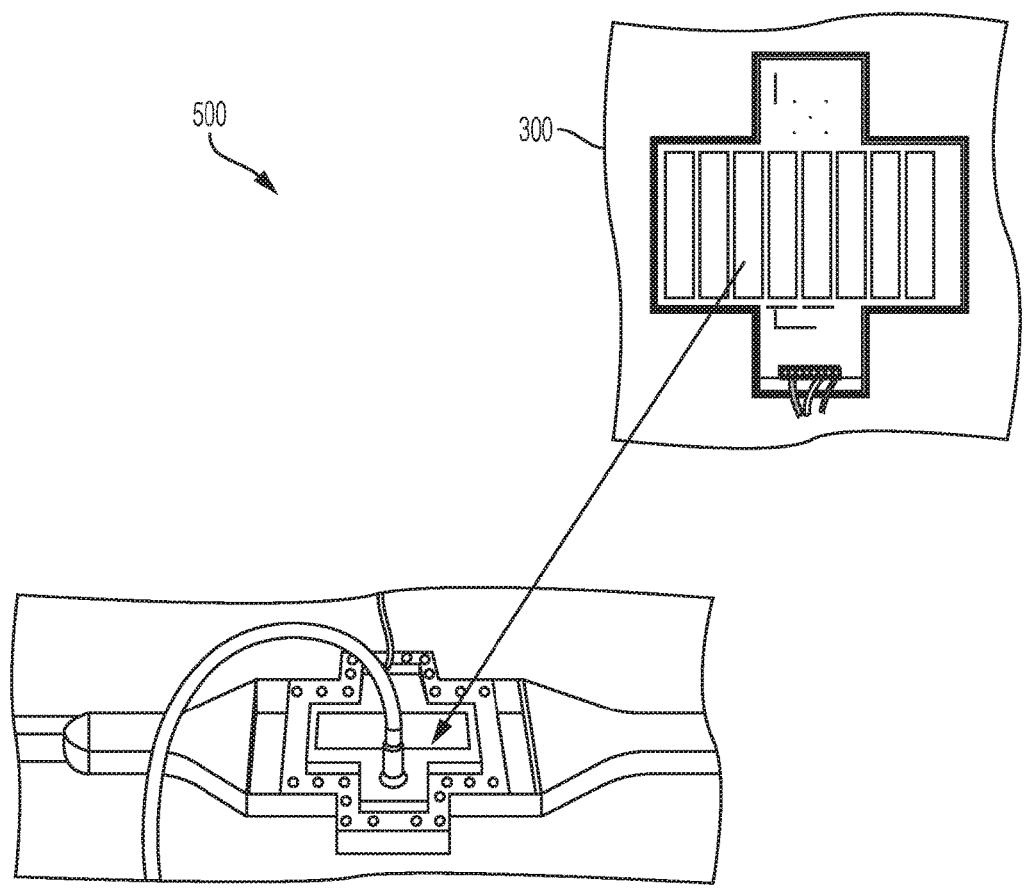
FIG. 5 is an image of a Miniature Electrical Aerosol Spectrometer (MEAS) with a first side of a classifier component shown in the inset, in accordance with an embodiment.
Figure 6:
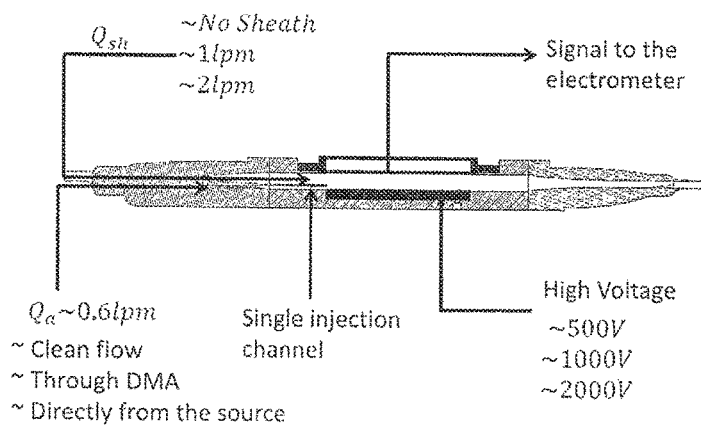
FIG. 6 is a schematic representation of a Miniature Electrical Aerosol Spectrometer, in accordance with an embodiment.

Referring to FIG. 5, in one embodiment, is a MEAS 500 with a collection component 300 (shown in inset), where the sensing circuitry is integrated with the collection plates 310 in the collection component 300. Referring to FIG. 6, in one embodiment, is a schematic representation of a side view of a MEAS 100 or 200.

Figure 7:
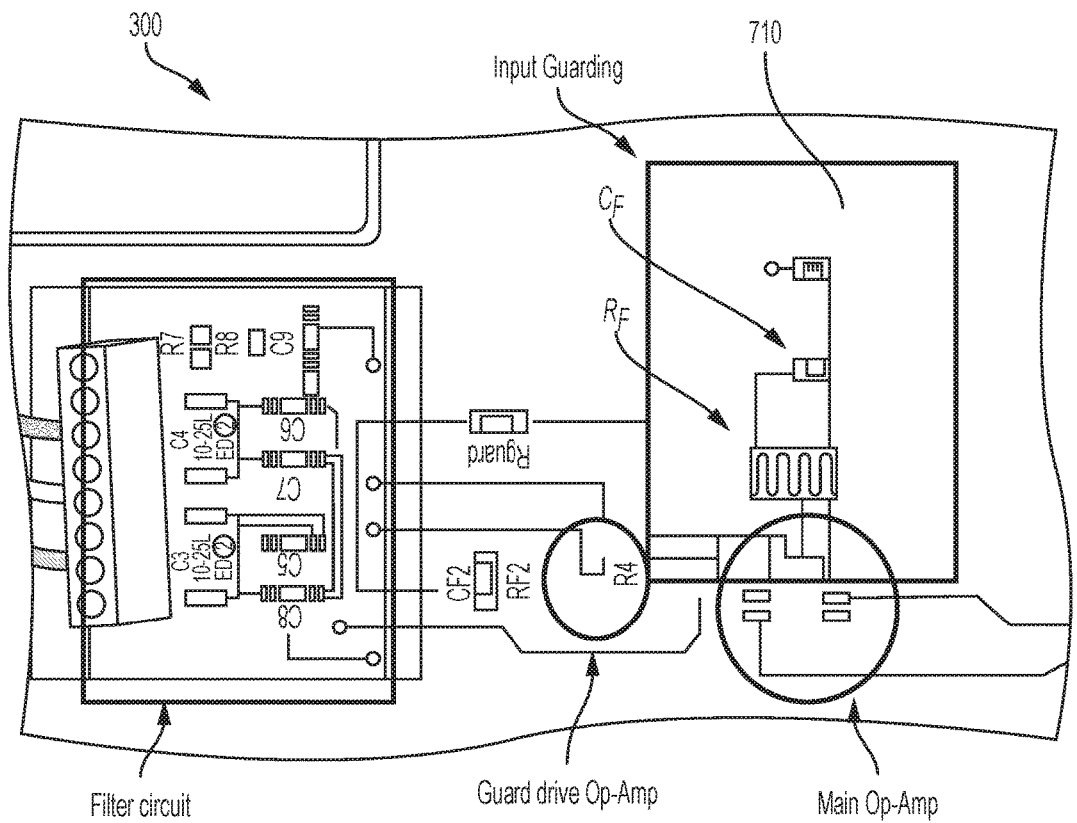
FIG. 7 is an image of a second side of a classifier component of a Miniature Electrical Aerosol Spectrometer, in accordance with an embodiment.

Referring to FIG. 7, in one embodiment, is a collection component 300 of a MEAS, where the sensing circuitry 710 is integrated with the collection plates 310 in the collection component 300.

Figure 8:
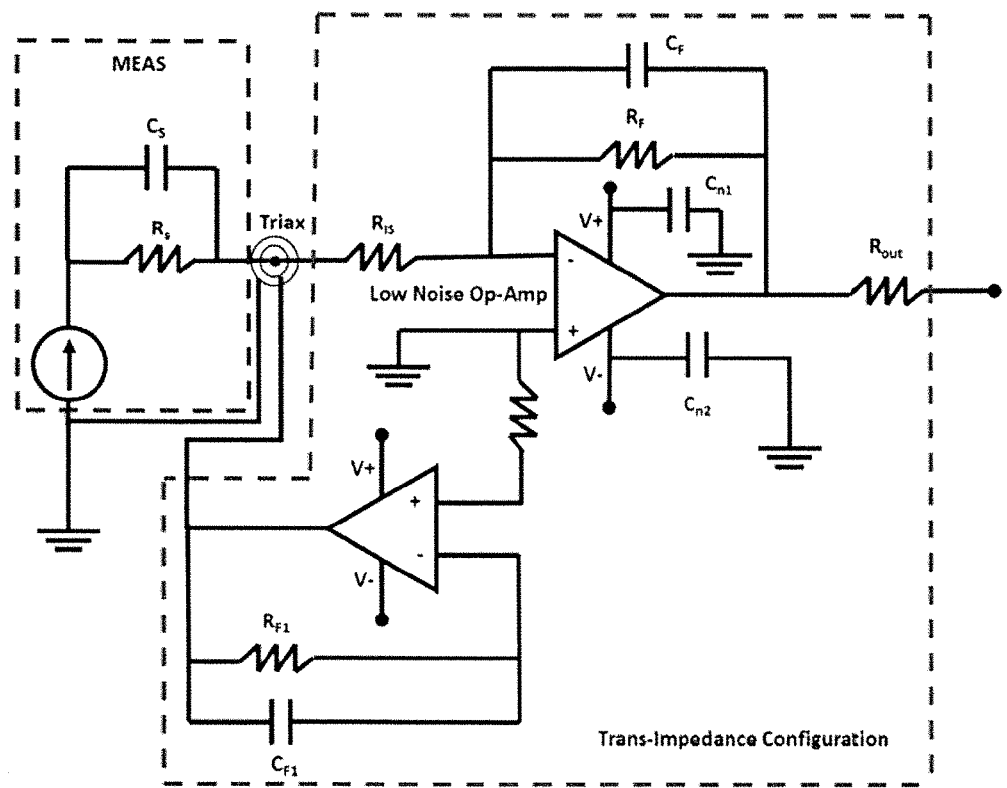
FIG. 8 is a schematic representation of sensing circuitry of a Miniature Electrical Aerosol Spectrometer, in accordance with an embodiment.

Referring to FIG. 8, in one embodiment, is a schematic diagram 800 of signal detection in a MEAS, although many other circuitry configurations are possible.

Figure 9:
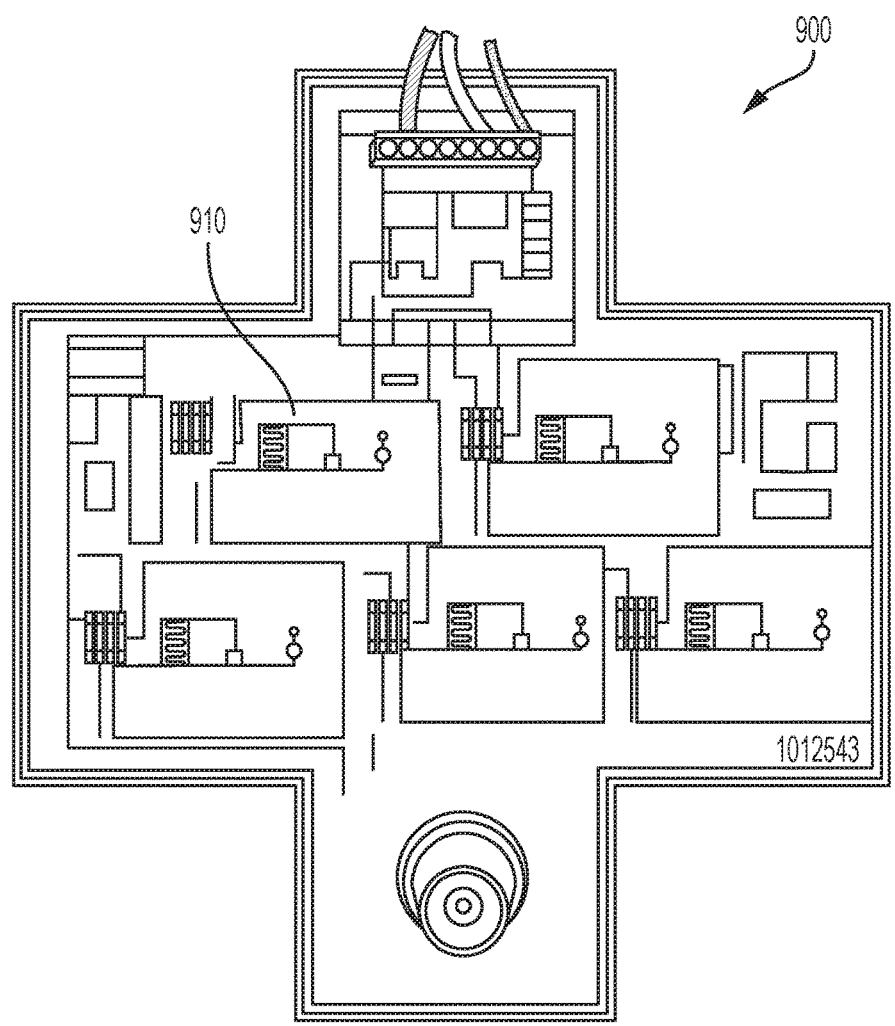
FIG. 9 is an image of a second side of a classifier component of a Miniature Electrical Aerosol Spectrometer, in accordance with an embodiment.

Referring to FIG. 9, in one embodiment, is a collection component 900 of a MEAS, where the sensing circuitry 910 is integrated with the collection plates 310 in the collection component 900. In this embodiment, the sensing circuitry 910 is a sensor array, which gives real-time size distribution measurements.

According to another embodiment, the miniature electrical-mobility aerosol spectrometer includes at least: an inlet section configured to receive particles to be evaluated by the spectrometer, a classifier section coupled to the inlet section, and an outlet section coupled to the classifier section. The classifier section, according to this embodiment, comprises a high voltage classifier plate positioned within the classifier section, and further includes two printed circuit boards. The first printed circuit board comprises the plurality of printed collection plates, and the second printed circuit board comprises the sensing circuitry. Many variations of this embodiment are possible.

Figure 10:
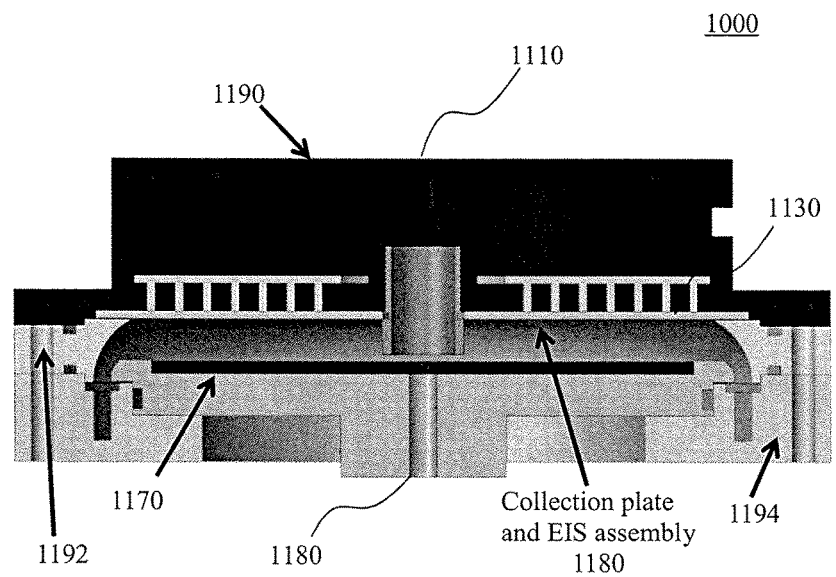
FIG. 10 is a schematic representation of a cutaway view of a Miniature Electrical Aerosol Spectrometer, in accordance with an embodiment.
Figure 11:
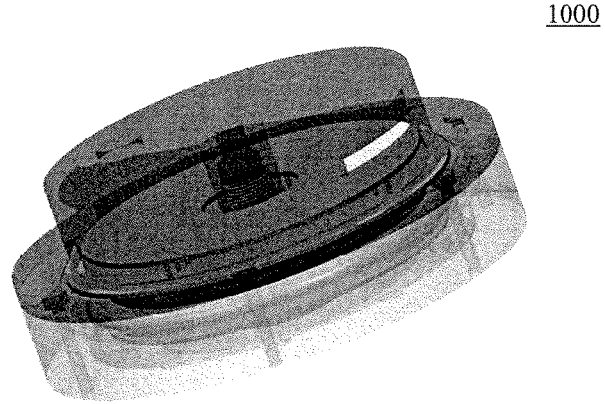
FIG. 11 is a schematic representation of a Miniature Electrical Aerosol Spectrometer, in accordance with an embodiment.

Referring to FIG. 10, in one embodiment, is a Miniature Electrical Aerosol Spectrometer (MEAS) 1000. The MEAS is round, compared to previous square and rectangular embodiments described herein. This embodiment further demonstrates that many different shapes, sizes, and cross-sections for the MEAS and components are possible. The MEAS 1000 comprises an inlet or input 1110, a classifier section 1130 with a collection plate 1180 and a high voltage plate 1170, and an outlet 1180. According to an embodiment, MEAS 1000 comprise a body with an aluminum cover 1190 which also functions as an RFI shield, Teflon housing 1192, and a steel housing 1194. However, many other body configurations and materials are possible. Referring to FIG. 11 is an exterior view of the MEAS 1000.

Figure 12:
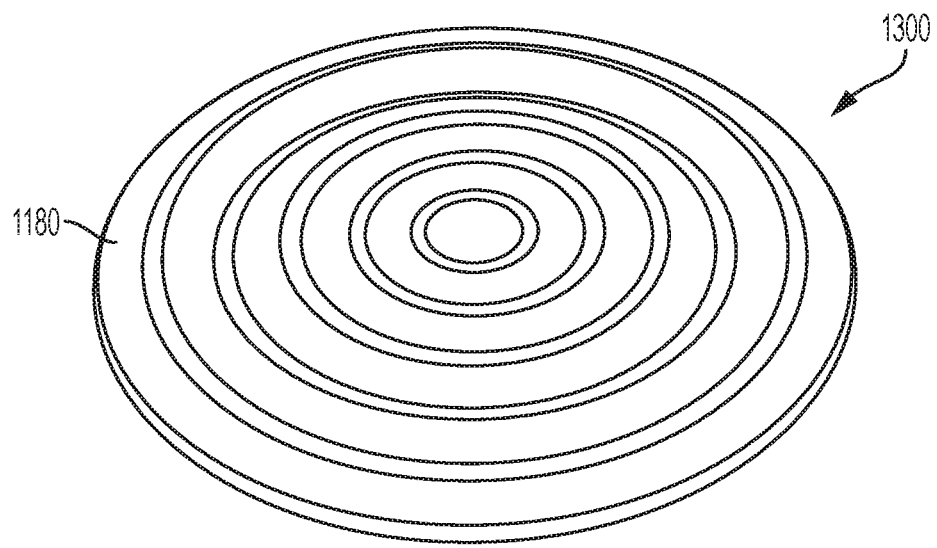
FIG. 12 is an image of a classifier component of a Miniature Electrical Aerosol Spectrometer, in accordance with an embodiment.
Figure 13:
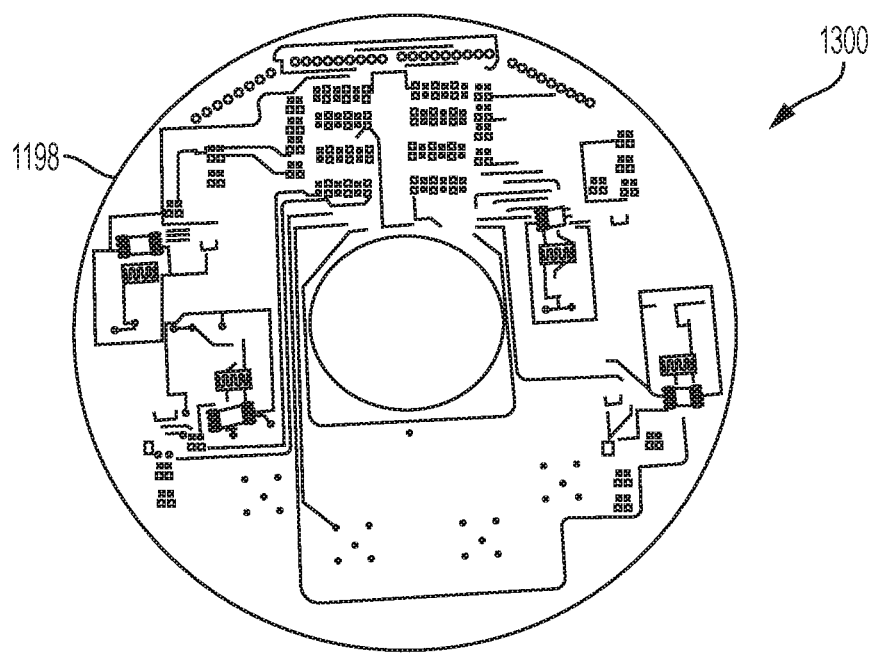
FIG. 13 is an image of a classifier component of a Miniature Electrical Aerosol Spectrometer, in accordance with an embodiment.

Referring to FIGS. 12 and 13 are both sides of a collection component 1300 with integrated sensing circuitry. In FIG. 12 is the first side of collection component 1300 with a series of round collection plates 1180. In FIG. 13 is the second side of collection component 1300 with sensing circuitry 1198. Although this collection component comprises four detection circuits, any number of detection circuits is possible.

Figure 14:
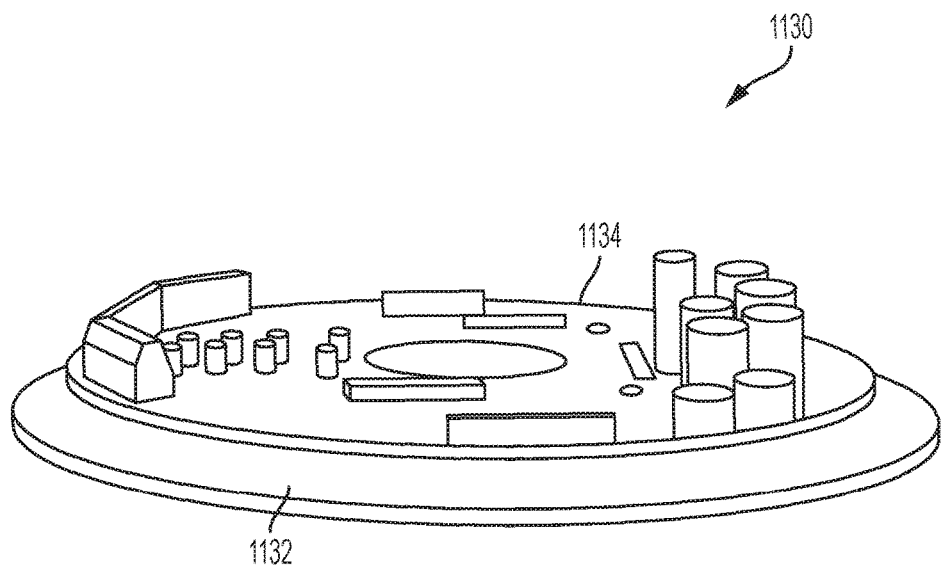
FIG. 14 is a side view image of a classifier component of a Miniature Electrical Aerosol Spectrometer, in accordance with an embodiment.

Referring to FIG. 14 is a round collection component 1300 for a round MEAS, where the collection component includes two printed circuit boards, a first circuit board 1132 with collection plates and a second circuit board 1134 comprising sensing circuitry. Accordingly, the printed circuit board described or otherwise envisioned herein may be a single circuit board, two circuit boards, or multiple circuit boards. The collection component 1300 optionally comprises one or more connectors for external electrometer measurements.

Figure 15:
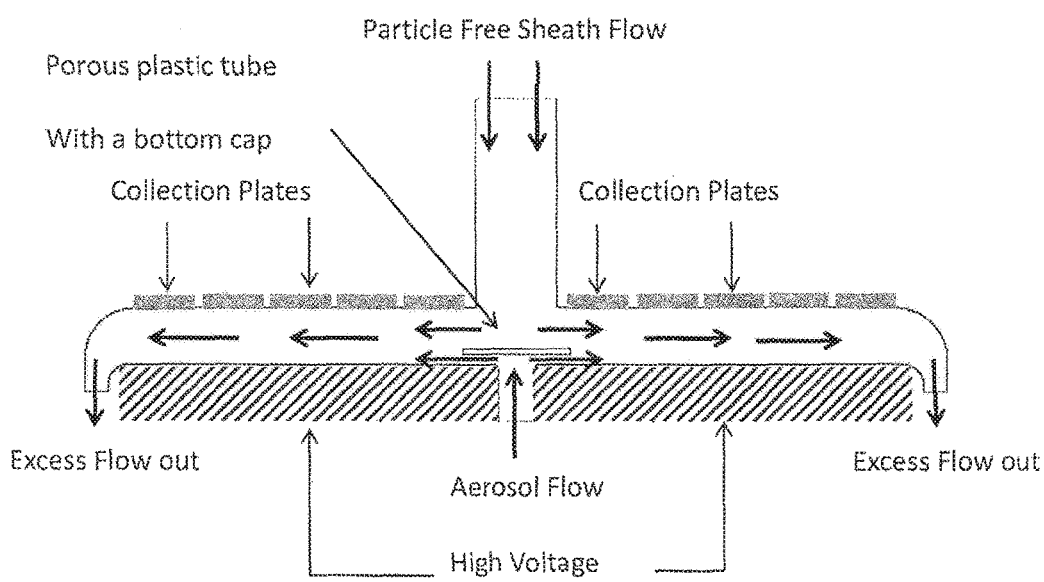
FIG. 15 is a schematic representation of a cutaway view of a round Miniature Electrical Aerosol Spectrometer, in accordance with an embodiment.

Referring to FIG. 14 is an embodiment of the round Miniature Electrical Aerosol Spectrometer (MEAS) 1000. FIG. 14 shows the flow of the particles through the upper portion of the MEAS, according to an embodiment. Referring to FIG. 15 is a schematic representation of a cutaway view of a round Miniature Electrical Aerosol Spectrometer, in accordance with an embodiment Accordingly, the MEAS embodiments as described or otherwise envisioned herein provide a compact, portable, inexpensive aerosol sizing instrument, optionally called a printed miniature electrical aerosol spectrometer (p-MEAS). The p-MEAS demonstrates that using 3D printing techniques and novel sensing approaches, particle size measurements can be significantly improved. Indeed, this new low-cost, portable detector system detects currents in the sub 5 fA level. Further, the radial version of the instrument (called r-MEAS) enables measurement of particle size distributions over a broader range of sizes.

According to an embodiment, therefore, the precise printing of an aerosol collector of different shapes is possible, as described or otherwise envisioned herein. Particles of selected sizes can be collected on the collectors using electrical fields or other force fields. An electrical connection can be provided to the collector to extract electrical current from the collected particles or detect the net charge collected in each collection plate. Further, a single printed plate can both collect particles and output net collected charge. The shape of the collector can be optimized to provide size-independent measures such as total number concentration, surface-area concentration, lung-deposited fraction, mass concentration, and so on. Integration with an optical sensor will allow for size-dependent measurements to sizes as large as 2.5 micron.

Although the present invention has been described in connection with a preferred embodiment, it should be understood that modifications, alterations, and additions can be made to the invention without departing from the scope of the invention as defined by the claims.

What is claimed is:

1. A miniature electrical-mobility aerosol spectrometer comprising:
   a single inlet section configured to receive particles to be evaluated by the spectrometer;
   an electrostatic precipitator section, wherein the inlet section is coupled to the electrostatic precipitator section;
   a classifier section, wherein the electrostatic precipitator section is coupled to the classifier section, and further wherein the classifier comprises a high voltage classifier plate and an opposing classifier component;
   a sensing circuitry coupled to the classifier component and configured to detect particles in the classifier section; and
   an outlet, wherein the classifier section is coupled to the outlet;
   wherein the classifier component comprises a two-sided printed circuit board,
   wherein the two-sided printed circuit board comprises the sensing circuitry, and wherein a first side of the two-sided printed circuit board comprises a plurality of printed collection plates.

2. The spectrometer of claim 1, wherein the miniature electrical-mobility aerosol spectrometer comprises a 3D-printed body.

3. The spectrometer of claim 1, wherein the electrostatic precipitator section comprises multiple channels.

4. The spectrometer of claim 1, wherein the electrostatic precipitator section comprises a single channel.

5. The spectrometer of claim 1, wherein each of the plurality of printed collection plates is rectangular.

6. The spectrometer of claim 1, wherein each of the plurality of printed collection plates is round.

7. The spectrometer of claim 1, wherein each collection plate is spaced from its respective one or more neighboring collection plates.

8. The spectrometer of claim 1, wherein a second side of the two-sided printed circuit board comprises a high sensitivity electric current detection circuit.

9. The spectrometer of claim 1, wherein a current signal from a second side of the two-sided printed circuit board is processed by a processor to record a signal and calculate particle concentration.

10. The spectrometer of claim 1, wherein the shape of each of the plurality of printed collection plates results in a sensor response with a predetermined particle size dependence.

11. A miniature electrical-mobility aerosol spectrometer comprising:
 a 3D-printed body comprising:
  (i) a single inlet section configured to receive particles to be evaluated by the spectrometer;
  (ii) an electrostatic precipitator section, wherein the inlet section is coupled to the electrostatic precipitator section;
  (iii) a classifier section, wherein the electrostatic precipitator section is coupled to the classifier section; and
  (iv) an outlet, wherein the classifier section is coupled to the outlet;
 a high voltage classifier plate positioned within the classifier section; and
 a classifier component positioned within the classifier section opposite the high voltage classifier plate, wherein the classifier component comprises sensing circuitry configured to detect particles in the classifier section, and wherein the classifier section comprises a two-sided printed circuit board, wherein the two-sided printed circuit board comprises the sensing circuitry, and wherein a first side of the two-sided printed circuit board comprises a plurality of printed collection plates.

12. The spectrometer of claim 11, wherein the electrostatic precipitator section comprises multiple channels.

13. The spectrometer of claim 11, wherein the electrostatic precipitator section comprises a single channel.

14. The spectrometer of claim 11, wherein each of the plurality of printed collection plates is rectangular.

15. The spectrometer of claim 11, wherein each of the plurality of printed collection plates is round.

16. The spectrometer of claim 11, wherein each collection plate is spaced from its respective one or more neighboring collection plates.

17. A miniature electrical-mobility aerosol spectrometer comprising:
 a round body comprising:
  (i) a single inlet section configured to receive particles to be evaluated by the spectrometer;
  (ii) an electrostatic precipitator section, wherein the inlet section is coupled to the electrostatic precipitator section;
  (iii) a classifier section, wherein the electrostatic precipitator section is coupled to the classifier section; and
  (iv) an outlet, wherein the classifier section is coupled to the outlet;
 a high voltage classifier plate positioned within the classifier section; and
 a round classifier component positioned within the classifier section opposite the high voltage classifier plate, wherein the round classifier component comprises sensing circuitry configured to detect particles in the round classifier section, and wherein the round classifier section comprises a round printed circuit board, wherein the printed circuit board comprises a plurality of printed collection plates.

18. The spectrometer of claim 17, wherein the one side of the round printed circuit board comprises the sensing circuitry.

19. The spectrometer of claim 17, wherein the miniature electrical-mobility aerosol spectrometer comprises a 3D-printed body.

20. The spectrometer of claim 17, wherein each collection plate is spaced from its respective one or more neighboring collection plates.

* * * * *